US011278558B2

(12) United States Patent
Vigsnæs et al.

(10) Patent No.: US 11,278,558 B2
(45) Date of Patent: Mar. 22, 2022

(54) SYNTHETIC COMPOSITION FOR MICROBIOTA MODULATION

(71) Applicant: Glycom A/S, Hørsholm (DK)

(72) Inventors: Louise Kristine Vigsnæs, Copenhagen (DK); Bruce McConnell, La Tour de Peilz (CH)

(73) Assignee: Glycom A/S, Hørsholm (DK)

( * ) Notice: Subject to any disclaimer, the term of this patent is extended or adjusted under 35 U.S.C. 154(b) by 92 days.

(21) Appl. No.: 16/490,027

(22) PCT Filed: Mar. 1, 2018

(86) PCT No.: PCT/DK2018/050041
§ 371 (c)(1),
(2) Date: Aug. 29, 2019

(87) PCT Pub. No.: WO2018/157900
PCT Pub. Date: Sep. 7, 2018

(65) Prior Publication Data
US 2020/0069709 A1   Mar. 5, 2020

(30) Foreign Application Priority Data

Mar. 1, 2017  (DK) .......................... PA 2017 70149

(51) Int. Cl.
*A61K 31/702* (2006.01)
*A23L 33/125* (2016.01)
*A23L 33/135* (2016.01)
*A61P 1/00* (2006.01)
*A61K 31/7004* (2006.01)

(52) U.S. Cl.
CPC .......... *A61K 31/702* (2013.01); *A23L 33/125* (2016.08); *A23L 33/135* (2016.08); *A61K 31/7004* (2013.01); *A61P 1/00* (2018.01)

(58) Field of Classification Search
None
See application file for complete search history.

(56) References Cited

U.S. PATENT DOCUMENTS

| | | |
|---|---|---|
| 2012/0171165 A1 | 7/2012 | Buck et al. |
| 2014/0335065 A1 | 11/2014 | Davis et al. |
| 2015/0238508 A1 | 8/2015 | Hernandez et al. |
| 2016/0243138 A1 | 8/2016 | Hennet et al. |
| 2016/0287619 A1 | 10/2016 | Vigsnaes et al. |
| 2016/0310514 A1 | 10/2016 | Salomonnsson et al. |
| 2016/0346303 A1 | 12/2016 | Hennet et al. |

FOREIGN PATENT DOCUMENTS

| | | |
|---|---|---|
| EP | 2708145 A1 | 3/2014 |
| EP | 2842560 A1 | 3/2015 |
| WO | 01/04341 A1 | 1/2001 |
| WO | 2010/115934 A1 | 10/2010 |
| WO | 2010/115935 A1 | 10/2010 |
| WO | 2011/100979 A1 | 8/2011 |
| WO | 2011/100980 A1 | 8/2011 |
| WO | 2012/007588 A9 | 1/2012 |
| WO | 2012/113404 A1 | 8/2012 |
| WO | 2012/113405 A1 | 8/2012 |
| WO | 2012/127410 A1 | 9/2012 |
| WO | 2012/155916 A1 | 11/2012 |
| WO | 2012/156897 A1 | 11/2012 |
| WO | 2012/156898 A1 | 11/2012 |
| WO | 2013/044928 A1 | 4/2013 |
| WO | 2013/091660 A1 | 6/2013 |
| WO | 2013/139344 A1 | 9/2013 |
| WO | 2016/066175 A1 | 5/2016 |
| WO | 2016/091265 A1 | 6/2016 |
| WO | 2016138911 A1 | 9/2016 |
| WO | 2017/021476 A1 | 2/2017 |
| WO | 2017/046711 A1 | 3/2017 |
| WO | 2007/101862 A1 | 9/2017 |

OTHER PUBLICATIONS

Thongaram, T., Hoeflinger, J. L., Chow, J., & Miller, M. J. (2017). Human milk oligosaccharide consumption by probiotic and human-associated bifidobacteria and lactobacilli. Journal of dairy science, 100(10), 7825-7833. (Year: 2017).*
LoCascio, R. G., Ninonuevo, M. R., Freeman, S. L., Sela, D. A., Grimm, R., Lebrilla, C. B., ... & German, J. B. (2007). Glycoprofiling of bifidobacterial consumption of human milk oligosaccharides demonstrates strain specific,...Journal of agricultural and food chemistry, 55(22), 8914-8919. (Year: 2007).*
Sela, D. A., & Mills, D. A. (2010). Nursing our microbiota: molecular linkages between bifidobacteria and milk oligosaccharides. Trends in microbiology, 18(7), 298-307. (Year: 2010).*
PCT/DK2018/050041, "International Search Report", PCT, dated Apr. 11, 2018, pp. 1-7.
PCT/DK2018/050041, "Written Opinion of the International Searching Authority", dated Apr. 11, 2018, pp. 1-10.
EPO, "Extended European Search Report", dated Nov. 23, 2020, pp. 1-9.
E. Elison et al., "Oral supplementation of healthy adults with 2'-O-fucosyllactose and lacto-N-neotetraose is well tolerated and shifts the intestinal microbiota", British Journal of Nutrition, pp. 1356-1368, Oct. 10, 2016.
M. Haarman et al., "Quantitative Real-Time PCR Assays to Identify and Quantify Fecal Bifidobacterium Species in Infants Receiving a Prebiotic Infant Formula", Applied and Environmental Microbiology, vol. 71, No. 5, pp. 2318-2324, May 5, 2005.
M. Chichlowski et al., "Bifidobacteria isolated from infants and cultured on human milk oligosaccharides affect intestinal epithelial function", J Pediatr Gastroenterol Nutr. Sep. 2012; 55(3):, pp. 321-327.

(Continued)

*Primary Examiner* — Dale R Miller
(74) *Attorney, Agent, or Firm* — Kunzler Bean & Adamson

(57) ABSTRACT

The invention relates to a method and composition for modulating the microbiota in the gastro-intestinal tracts of non-infant humans, particularly for increasing the abundance of *Bifidobacterium longum* and/or *Bifidobacterium bifidum* in the gut microbiota of non-infant humans.

20 Claims, No Drawings

(56) References Cited

OTHER PUBLICATIONS

AP Allen et al., "Bifidobacterium longum 1714 as a translational psychobiotic: modulation of stress, electrophysiology and neurocognition in healthy volunteers", Translational Psychiatry (2016), Nov. 1, 2016, pp. 1-7.

F. Bottacini et al., "Diversity, ecology and intestinal function of bifidobacteria", 11th International Symposium on Lactic Acid Bacteria Egmond aan Zee, the Netherlands, Aug. 31-Sep. 4, 2014, pp. 1-15.

A. Klindworth et al., "Evaluation of general 16S ribosomal RNA gene PCR primers for classical and next-generation sequencing-based diversity studies", Nucleic Acids Research, 2013, vol. 41, No. 1, Aug. 28, 2012, pp. 1-11.

S. Duranti et al., "Exploration of the Genomic Diversity and Core Genome of the Bifidobacterium adolescentis Phylogenetic Group by Means of a Polyphasic Approach", Applied and Environmental Microbiology vol. 79 No. 1, Jan. 2012, pp. 336-346.

Xi Chen, "Human Milk Oligosaccharides (HMOS): Structure, Function, and Enzyme-Catalyzed Synthesis", Advances in Carbohydrate Chemistry and Biochemistry, vol. 72 ISSN 0065-2318, 2015, pp. 113-190.

L. Bode, "Human milk oligosaccharides and their beneficial effects", Handbook of dietary and nutritional aspects of human breast milk Human Health Handbooks No. 5, 2013, pp. 515-531.

T. Urashima et al., "Milk Oligosaccharides", Nova Biomedical Books, 2011, pp. 1-99.

B. Strasser et al., "Probiotic Supplements Beneficially Affect Tryptophan—Kynurenine Metabolism and Reduce the Incidence of Upper Respiratory Tract Infections in Trained Athletes: A Randomized, Double-Blinded, Placebo-Controlled Trial", Nutrients 2016, Nov. 23, 2016, pp. 1-15.

C. Schwab, "Trophic Interactions of Infant Bifidobacteria and Eubacterium hallii during L-Fucose and Fucosyllactose Degradation", Frontiers in Microbiology vol. 8 | Article 95, Jan. 2017, pp. 1-14.

R.C. Edgar, "Uparse: highly accurate OTU sequences from microbial amplicon reads", 2013 Nature America, Inc vol. 10 No. 10, Aug. 18, 2013, pp. 996-1000.

* cited by examiner

SYNTHETIC COMPOSITION FOR MICROBIOTA MODULATION

FIELD OF THE INVENTION

This invention relates to a method and composition for modulating the microbiota in the gastro-intestinal tracts of non-infant humans, particularly for increasing the abundance of *Bifidobacterium longum* and/or *Bifidobacterium bifidum* in the gut microbiota of non-infant humans.

BACKGROUND OF THE INVENTION

It has been estimated that the human intestine harbours $10^{13}$ to $10^{14}$ bacterial cells and the number of bacteria outnumbers the total number of cells in the body by a factor of 10. The microbiota of the human intestine is a complex and very dynamic microbial ecosystem, which is considered to serve numerous important functions for its human host, including protection against pathogens, induction of immune regulatory functions, nutrient processing and metabolic functions. The intestinal microbiota consists of various populations, which are important to preserve human health, and recent research has been able to link imbalances in the intestinal bacterial population to both intestinal and extra-intestinal inflammatory diseases.

Selective stimulation of specific intestinal bacteria to promote their growth and metabolic activity could be a helpful approach in creating a benign intestinal microbial community. Because some bacteria are able to produce a large selection of carbohydrate active enzymes (such as glycoside-hydrolases and transporters), the bacteria can grow on carbon sources, which may be less easily used by other members of the intestinal microbial community.

Human milk oligosaccharides (HMOs) are a heterogeneous mixture of soluble glycans found in human milk. They are the third most abundant solid component after lactose and lipids in human milk and are present in concentrations of 5-25 g/l (Bode: *Human milk oligosaccharides and their beneficial effects* in: Handbook of dietary and nutritional aspects of human breast milk (Eds. Zibadi et al.) pp. 515-31, Wageningen Academic Publishers (2013)). HMOs are resistant to enzymatic hydrolysis in the small intestine and are thus largely undigested and unabsorbed. The majority of HMOs that reach the colon serve as substrates to shape the gut ecosystem by selectively stimulating the growth of specific bacteria. HMOs are believed to substantially modulate the infant gut microbiota and play a decisive role in the differences in the microbiota of formula-fed and breast-fed infants. These differences include the predominance of *Bifidobacterium* in the gut of breast-fed infants compared to a more diverse gut microbiota in formula-fed infants. This is viewed as beneficial for the infant because strains of *Bifidobacterium* species are believed to have a positive effect on gut health (Chichlowski et al. *J. Pediatr. Gastroenterol. Nutr.* 55, 321 (2012)). However, it is not known if HMOs can stimulate the growth of bifidobacteria in the adult human intestine and specifically change the *Bifidobacterium* species composition.

Bifidobacteria are considered one of the most beneficial probiotics. As an example, strains of *B. bifidum* and *B. longum* have been widely studied for their immunomodulatory properties and protecting effect by suppressing pathogens. Species of *Bifidobacterium* grown on HMOs have shown to down regulate expression of virulence genes from pathogenic bacteria such as *E. coli* O157 and *Salmonella enterica* serovar *Typhimurium*, and affect epithelial cell function by regulating immune gene expression and tight junction (Chichlowski et al. *J. Pediatr. Gastroenterol. Nutr.* 55, 321 (2012)). Bifidobacteria are also able to affect the gut/brain axis; for example by impacting tryptophan (an important metabolite for the gut and brain interaction). It has been shown that *B. bifidum* combined with other probiotic bacteria can impact tryptophan levels in blood. An inverse correlation of serum levels of tryptophan with concentration of faecal calprotectin, a marker for gut permeability, has been reported in patients suffering from Alzheimer's disease, thus indicating a close relationship between the intestinal barrier function and tryptophan concentration in blood (Strasser et al. *Nutrients* 8, 752 (2016)). Additionally, consumption of *B. longum* is associated with reduced stress and improved memory (Allen et al. *Transl. Psychiatry* 6, e939 (2016)).

Metabolic end products such as short chain fatty acids (acetate, propionate and butyrate), produced during carbohydrate fermentation, also contribute to intestinal functionality and probiotic attributes of bifidobacteria. It has previously been shown that acetate produced by bifidobacteria can enhance intestinal defence mediated by epithelial cells and thereby protect the host against assault. In addition, while bifidobacteria do not produce butyrate as an end product of fermentation, the importance of metabolic cross-feeding on acetate by butyrate-producing bacteria in the gut has been demonstrated. A study has shown that the butyrate-producing species *E. hallii* can utilize intermediates of bifidobacterial HMO fermentation, such as acetate and lactate, and produce butyrate (Schwab et al. *Front. Microbiol.* 8:95 (2017)). Butyrate is the primary energy source for colonocytes and has been reported to regulate the physical and functional integrity of the normal colonic mucosa by altering mucin gene expression.

There is a need, therefore, for means, preferably orally or enterally administered means, more preferably dietetic means, for effectively increasing the abundance, particularly the relative abundance, of bifidobacteria, in particular that of *Bifidobacterium longum* and/or *Bifidobacterium bifidum*, in the microbiota of the gastro-intestinal tracts of humans, preferably non-infant humans.

SUMMARY OF THE INVENTION

A first aspect of this invention relates to an HMO, advantageously a neutral HMO, for use in the delayed increase in the abundance, particularly the relative abundance, of a *Bifidobacterium longum* and/or *Bifidobacterium bifidum*, in the microbiota in the gastro-intestinal tract of a non-infant human. Preferably, the HMO, advantageously a neutral HMO, is for use in the delayed increase the abundance of *Bifidobacterium longum* and/or *Bifidobacterium bifidum*, in the gastro-intestinal tract of a non-infant human to treat or prevent in the non-infant human:
   an enteropathogenic infection,
   type 2 diabetes and/or obesity,
   impaired gut barrier function,
   brain gut disorders such as stress, anxiety and depressive like behaviour,
   allergies, and/or
   an inflammation related to a gastro-intestinal condition.

More preferably, the neutral HMO is a fucosylated neutral HMO, such as 2'-FL, 3-FL or DFL, or a mixture thereof, a non-fucosylated neutral HMO, such as LNnT or LNT, or a mixture thereof, especially a mixture of a fucosylated and a non-fucosylated neutral HMO.

A second aspect of the invention is a synthetic composition comprising an HMO, advantageously a neutral HMO, for use in the delayed increase in the abundance, particularly the relative abundance, of *Bifidobacterium longum* and/or *Bifidobacterium bifidum*, in the microbiota in the gastro-intestinal tract of a non-infant human, preferably to treat or prevent in the non-infant human:
- an enteropathogenic infection,
- type 2 diabetes and/or obesity,
- impaired gut barrier function,
- brain gut disorders such as stress, anxiety and depressive like behaviour,
- allergies, and/or
- an inflammation related to a gastro-intestinal condition.

The synthetic composition can be a nutritional or pharmaceutical composition.

Preferably, the neutral HMO is a fucosylated neutral human milk oligosaccharide, such as 2'-FL, 3-FL or DFL, a non-fucosylated neutral human milk oligosaccharide, such as LNnT or LNT, or especially a mixture of both.

A third aspect of this invention is a method for increasing the abundance, particularly the relative abundance, of *Bifidobacterium longum* and/or *Bifidobacterium bifidum*, in the microbiota in the gastro-intestinal tract of a non-infant human, the method comprising orally or enterally administering to the non-infant human for a period of at least 14 days an effective amount of a human milk oligosaccharide, advantageously a neutral HMO.

A fourth aspect of this invention is a method for the prophylaxis or treatment of an enteropathogenic infection in a non-infant human, the method comprising orally or enterally administering to the non-infant human for a period of at least 14 days, an amount of one or more human milk oligosaccharides, advantageously neutral HMOs, effective to preferentially increase the abundance, particularly the relative abundance, of *Bifidobacterium longum* and/or *Bifidobacterium bifidum*, in the microbiota in the gastro-intestinal tract of the non-infant human.

A fifth aspect of this invention is a method for the prophylaxis or treatment of a non-infant human having type 2 diabetes and/or obesity, the method comprising orally or enterally administering to the non-infant human for a period of at least 14 days, an amount of one or more human milk oligosaccharides, advantageously neutral HMOs, effective to preferentially increase the abundance, particularly the relative abundance, of *Bifidobacterium longum* and/or *Bifidobacterium bifidum*. Preferably, the amount is effective to preferentially increase the abundance of *Bifidobacterium longum* and/or *Bifidobacterium bifidum*, sufficiently to improve intestinal permeability and/or increase insulin sensitivity.

A sixth aspect of this invention is a method for the prophylaxis or treatment of a non-infant human having an inflammation related gastro-intestinal condition or an allergy, the method comprising orally or enterally administering to the non-infant human for a period of at least 14 days, an amount of one or more human milk oligosaccharides, advantageously neutral HMOs, effective to preferentially increase the abundance, particularly the relative abundance, of *Bifidobacterium longum* and/or *Bifidobacterium bifidum*. The gastro-intestinal condition may be intestinal bowel disease or irritable bowel syndrome. Preferably, the amount is effective to preferentially increase the abundance of *Bifidobacterium longum* and/or *Bifidobacterium bifidum*, sufficiently to induce an anti-inflammatory immune response.

A seventh aspect of this invention is a method for the prophylaxis or treatment of a non-infant human having a brain gut disorder, the method comprising orally or enterally administering to the non-infant human for a period of at least 14 days, an amount of one or more human milk oligosaccharides, advantageously neutral HMOs, effective to preferentially increase the abundance, particularly the relative abundance, of *Bifidobacterium longum* and/or *Bifidobacterium bifidum*. The brain gut disorder may be stress, anxiety and depressive like behaviour.

An eighth aspect of this invention is method for modulating the bifidobacterial composition of the gastrointestinal microbiota of a non-infant human, the method comprising enterally, preferably orally, administering to the non-infant human:
(a) in a first step for a period of 14 days or less:
   an effective amount of a human milk oligosaccharide, preferably a neutral human milk oligosaccharide, or
   a synthetic composition comprising an effective amount of a human milk oligosaccharide, preferably a neutral human milk oligosaccharide
to increase the abundance, particularly the relative abundance, of a *Bifidobacterium* of the *Bifidobacterium adolescentis* phylogenetic group in the microbiota in the gastro-intestinal tract of the non-infant human, and
(b) in a second step for an additional period:
   an effective amount of a human milk oligosaccharide, preferably a neutral human milk oligosaccharide, or
   a synthetic composition comprising an effective amount of a human milk oligosaccharide, preferably a neutral human milk oligosaccharide
to increase the abundance, particularly the relative abundance, of *Bifidobacterium longum* and/or *Bifidobacterium bifidum* in the microbiota in the gastro-intestinal tract of the non-infant human, wherein the period of the first step and the additional period of the second step together are at least 14 days.

Preferably, in the third to eighth aspects of the invention, the HMO is administered for at least 21 days.

A ninth aspect of this invention is the use of an HMO, advantageously a neutral HMO, or a synthetic composition containing a HMO, advantageously a neutral HMO, in increasing the abundance of *Bifidobacterium longum* and/or *Bifidobacterium bifidum*, in the microbiota in the gastro-intestinal tract of a non-infant human in a delayed manner, preferably to treat or prevent in the non-infant human
- an enteropathogenic infection,
- type 2 diabetes and/or obesity,
- impaired gut barrier function,
- brain gut disorders such as stress, anxiety and depressive like behaviour,
- allergy, and/or
- an inflammation related to a gastro-intestinal condition.

DETAILED DESCRIPTION OF THE INVENTION

It has now been surprisingly found by that administration of one or more human milk oligosaccharides to non-infant children and adults, for a period of at least 14 days, preferentially increases the abundance of a *Bifidobacterium longum* and/or *Bifidobacterium bifidum*, in the microbiota of their gastro-intestinal tract. It has been previously reported in WO 2016/138911 that the administration of one or more HMOs to a non-infant human increases the abundance of bifidobacteria of the *B. adolescentis* phylogenetic group, especially *Bifidobacterium adolescentis* and/or *Bifidobacte-*

*rium pseudocatenulatum*. This increase in the bifidobacteria of the *B. adolescentis* phylogenetic group is temporary and lasts about 14 days. Thereafter, upon prolonged administration of the one or more HMOs, the abundance of *Bifidobacterium longum* and/or *Bifidobacterium bifidum* surprisingly increases.

Thus it has been discovered that human milk oligosaccharides can, by oral or enteral ingestion, modulate the non-infant human intestinal microbiota by preferentially promoting the growth of the species of *Bifidobacterium longum* and/or *Bifidobacterium bifidum*, and increase the abundance of this/these species in the non-infant human intestine. As an outcome, a more benign intestinal microbial community can be shaped and maintained, and by the increased abundance of a *Bifidobacterium longum* and/or *Bifidobacterium bifidum*, pathogenic infections can be inhibited and intestinal and extra-intestinal diseases can be prevented or improved.

Herein, the following terms have the following meanings:

"Delayed increase" means an increase after a period of about 14 days. In this regard, "delayed increase in the abundance of *Bifidobacterium longum* and/or *Bifidobacterium bifidum*" means that, after commencing the HMO administration to the patient, that increase occurs only after about 14 days.

"Non-infant human" or "non-infant" preferably means a human of 3 years of age and older. A non-infant human can be a child, a teenager, an adult or an elderly.

"Human milk oligosaccharide" or "HMO" preferably means a complex carbohydrate found in human breast milk (Urashima et al.: *Milk Oligosaccharides*. Nova Science Publisher (2011); Chen *Adv. Carbohydr. Chem. Biochem.* 72, 113 (2015)). The HMOs have a core structure comprising a lactose unit at the reducing end that can be elongated by one or more β-N-acetyl-lactosaminyl and/or one or β-more lacto-N-biosyl units, and which core structure can be substituted by an α L-fucopyranosyl and/or an α-N-acetyl-neuraminyl (sialyl) moiety. In this regard, the non-acidic (or neutral) HMOs are devoid of a sialyl residue, and the acidic HMOs have at least one sialyl residue in their structure. The non-acidic (or neutral) HMOs can be fucosylated or non-fucosylated. Examples of such neutral non-fucosylated HMOs include lacto-N-tetraose (LNT), lacto-N-neotetraose (LNnT), lacto-N-neohexaose (LNnH), para-lacto-N-neohexaose (pLNnH), para-lacto-N-hexaose (pLNH) and lacto-N-hexaose (LNH). Examples of neutral fucosylated HMOs include 2'-fucosyllactose (2'-FL), lacto-N-fucopentaose I (LNFP-I), lacto-N-difucohexaose I (LNDFH-I), 3-fucosyllactose (3-FL), difucosyllactose (DFL), lacto-N-fucopentaose II (LNFP-II), lacto-N-fucopentaose III (LNFP-III), lacto-N-difucohexaose III (LNDFH-III), fucosyl-lacto-N-hexaose II (FLNH-II), lacto-N-fucopentaose V (LNFP-V), lacto-N-fucopentaose VI (LNFP-VI), lacto-N-difucohexaose II (LNDFH-II), fucosyl-lacto-N-hexaose I (FLNH-I), fucosyl-para-lacto-N-hexaose I (FpLNH-I), fucosyl-para-lacto-N-neohexaose II (F-pLNnH II) and fucosyl-lacto-N-neohexaose (FLNnH). Examples of acidic HMOs include 3'-sialyllactose (3'-SL), 6'-sialyllactose (6'-SL), 3-fucosyl-3'-sialyllactose (FSL), LST a, fucosyl-LST a (FLST a), LST b, fucosyl-LST b (FLST b), LST c, fucosyl-LST c (FLST c), sialyl-LNH (SLNH), sialyl-lacto-N-hexaose (SLNH), sialyl-lacto-N-neohexaose I (SLNH-I), sialyl-lacto-N-neohexaose II (SLNH-II) and disialyl-lacto-N-tetraose (DSLNT).

"Synthetic composition" means a composition which is artificially prepared and preferably means a composition containing at least one compound that is produced ex vivo chemically and/or biologically, e.g. by means of chemical reaction, enzymatic reaction or recombinantly. In some embodiments a synthetic composition of the invention may be, but preferably is not, identical with a naturally occurring composition. The synthetic composition typically comprises one or more compounds, advantageously HMOs, that are capable of preferentially increasing the abundance of *Bifidobacterium longum* and/or *Bifidobacterium bifidum*, in the microbiota of the gastro-intestinal tract when administered for a period of at least 14 days. In some embodiments the synthetic composition may comprise one or more compounds or components other than HMOs that may have an effect on bifidobacteria of a non-infant human subject microbiota in vivo, e.g. non-digestible oligosaccharides or prebiotics. Also in some embodiments, the synthetic compositions may comprise one or more nutritionally or pharmaceutically active components which do not affect adversely the efficacy of the above mentioned compounds. Some non-limiting embodiments of a synthetic composition of the invention are also described below.

"Microbiota", "microflora" and "microbiome" preferably mean a community of living microorganisms that typically inhabits a bodily organ or part, particularly the gastro-intestinal organs of non-infant humans. The most dominant members of the gastrointestinal microbiota include microorganisms of the phyla of *Firmicutes, Bacteroidetes, Actinobacteria, Proteobacteria, Synergistetes, Verrucomicrobia, Fusobacteria,* and *Euryarchaeota*; at genus level *Bacteroides, Faecalibacterium, Bifidobacterium, Roseburia, Alistipes, Collinsella, Blautia, Coprococcus, Ruminococcus, Eubacterium* and *Dorea*; at species level *Bacteroides uniformis, Alistipes putredinis, Parabacteroides merdae, Ruminococcus bromii, Dorea longicatena, Bacteroides caccae, Bacteroides thetaiotaomicron, Eubacterium hallii, Ruminococcus torques, Faecalibacterium prausnitzii, Ruminococcus lactaris, Collinsella aerofaciens, Dorea formicigenerans, Bacteroides vulgatus* and *Roseburia intestinalis*. The gastrointestinal microbiota includes the mucosa-associated microbiota, which is located in or attached to the mucus layer covering the epithelium of the gastrointestinal tract, and luminal-associated microbiota, which is found in the lumen of the gastrointestinal tract.

"Enteral administration" preferably means any conventional form for delivery of a composition to a non-infant that causes the deposition of the composition in the gastrointestinal tract (including the stomach). Methods of enteral administration include feeding through a naso-gastric tube or jejunum tube, oral, sublingual and rectal.

"Oral administration" preferably means any conventional form for the delivery of a composition to a non-infant through the mouth. Accordingly, oral administration is a form of enteral administration.

"Effective amount" preferably means an amount of a composition that provides an HMO in a sufficient amount to render a desired treatment outcome in a non-infant. An effective amount can be administered in one or more doses to achieve the desired treatment outcome.

"Relative abundance of a *Bifidobacterium longum* and/or *Bifidobacterium bifidum*" preferably means the abundance of a *Bifidobacterium longum* and/or *Bifidobacterium bifidum* relative to other bifidobacteria in the microbiota of the gastro-intestinal tract of non-infant humans.

"Relative growth of a *Bifidobacterium longum* and/or *Bifidobacterium bifidum*" preferably means the growth of a *Bifidobacterium longum* and/or *Bifidobacterium bifidum* relative to other bifidobacteria in the microbiota in the gastro-intestinal tract of non-infant humans.

"*Bifidobacterium* of the *B. adolescentis* phylogenetic group" means a bacterium selected from a group consisting of *Bifidobacterium* adolescentis, *Bifidobacterium* angulatum, *Bifidobacterium* catenulatum, *Bifidobacterium* pseudocatenulatum, *Bifidobacterium* kashiwanohense, *Bifidobacterium* dentum and *Bifidobacterium* stercoris (Duranti et al. *Appl. Environ. Microbiol.* 79, 336 (2013), Bottacini et al. *Microbial Cell Fact.* 13:S4 (2014)). Preferably a *Bifidobacterium* of the *B. adolescentis* phylogenetic group *is Bifidobacterium adolescentis* and/or *Bifidobacterium* pseudocatenulatum.

"Relative abundance of a *Bifidobacterium* of the *B. adolescentis* phylogenetic group" preferably means the abundance of a *Bifidobacterium* of the *B. adolescentis* phylogenetic group relative to other bifidobacteria in the microbiota of the gastro-intestinal tract of non-infants.

"Relative abundance of *B. adolescentis* and/or *B. pseudocatenulatum*" preferably means the abundance of *B. adolescentis* and/or *B. pseudocatenulatum* relative to other bifidobacteria in the microbiota of the gastro-intestinal tract of non-infants.

"Relative growth of a *Bifidobacterium* of the *B. adolescentis* phylogenetic group" preferably means the growth of a *Bifidobacterium* of the *B. adolescentis* phylogenetic group relative to other bifidobacteria in the microbiota in the gastro-intestinal tract of non-infants.

"Relative growth of *B. adolescentis* and/or *B. pseudocatenulatum*" preferably means the growth of *B. adolescentis* and/or *B. pseudocatenulatum* relative to other bifidobacteria in the microbiota in the gastro-intestinal tract of non-infants.

"Treat" means to address a medical condition or disease with the objective of improving or stabilising an outcome in the person being treated. Treat includes the dietary or nutritional management of the medical condition or disease by addressing nutritional needs of the person being treated. "Treating" and "treatment" have grammatically corresponding meanings.

In accordance with this invention, it has been discovered that an HMO, preferably a neutral HMO, can promote the growth, particularly the relative growth, of a *Bifidobacterium longum* and/or *Bifidobacterium bifidum*, in the microbiota in the gastro-intestinal tract of non-infants, when administered for at least 14 days, preferably more than 14 days. For this reason, an HMO can be used for (delayed) increasing the abundance, particularly the relative abundance, of a *Bifidobacterium longum* and/or *Bifidobacterium bifidum*, in the microbiota in the gastro-intestinal tract of non-infants. As a result, an HMO can be used for treating or preventing viral and/or bacterial infections (especially enteropathogenic infections), intestinal inflammatory diseases (especially IBS and IBD), allergies and gut-brain disorders and extra-intestinal diseases (especially obesity and type 2 diabetes) in non-infant humans.

Accordingly, the first aspect of the invention relates to an HMO, advantageously a neutral HMO, for use in the delayed increase in the abundance, particularly the relative abundance, of a *Bifidobacterium longum* and/or *Bifidobacterium bifidum*, in the microbiota in the gastro-intestinal tract of non-infant humans, and thereby treating and/or preventing viral and/or bacterial infections (especially enteropathogenic infections), intestinal inflammatory diseases (especially IBS and IBD), allergies and gut-brain disorders and extra-intestinal diseases (especially obesity and type 2 diabetes).

The neutral HMO can preferably be one or more fucosylated HMOs or one or more non-fucosylated HMOs. In one embodiment, the neutral HMO is a mixture neutral HMOs, even preferably a mixture comprising, essentially consisting of or consisting of a fucosylated and a non-fucosylated neutral HMO. Particularly, the mixture contains, essentially consisting of or consists of a fucosylated neutral HMO selected from the list consisting of 2'-FL, 3-FL, DFL, LNFP-I, LNFP-II, LNFP-III, LNFP-V, LNFP-VI, LNDFH-I, LNDFH-II, LNDFH-III, FLNH-I, FLNH-II, FLNnH, FpLNH-I and F-pLNnH II, and a non-fucosylated neutral HMO selected from the list consisting of LNT, LNnT, LNH, LNnH, pLNH and pLNnH. Especially, the mixture contains, essentially consists of or consists of a fucosylated neutral HMO selected from the list consisting of 2'-FL, 3-FL and DFL, and a non-fucosylated neutral HMO selected from the list consisting of LNT and LNnT, advantageously the mixture comprises, essentially consists of or consist of i) 2'-FL and LNnT, ii) 2'-FL and LNT or iii) 2'-FL, LNT and LNnT.

The HMOs suitable for use in the delayed increase in abundance, particularly the relative abundance, of a *Bifidobacterium longum* and/or *Bifidobacterium bifidum* in the microbiota in the gastro-intestinal tract of non-infants, can be isolated or enriched by well-known processes from milk(s) secreted by mammals including, but not limited to human, bovine, ovine, porcine, or caprine species. The HMOs can also be produced by well-known processes using microbial fermentation, enzymatic processes, chemical synthesis, or combinations of these technologies. As examples, using chemistry LNnT can be made as described in WO 2011/100980 and WO 2013/044928, LNT can be synthesized as described in WO 2012/155916 and WO 2013/044928, a mixture of LNT and LNnT can be made as described in WO 2013/091660, 2'-FL can be made as described in WO 2010/115934 and WO 2010/115935, 3-FL can be made as described in WO 2013/139344, 6'-SL and salts thereof can be made as described in WO 2010/100979, sialylated oligosaccharides can be made as described in WO 2012/113404 and mixtures of human milk oligosaccharides can be made as described in WO 2012/113405. As examples of enzymatic production, sialylated oligosaccharides can be made as described in WO 2012/007588, fucosylated oligosaccharides can be made as described in WO 2012/127410, and advantageously diversified blends of human milk oligosaccharides can be made as described in WO 2012/156897 and WO 2012/156898. With regard to biotechnological methods, WO 01/04341 and WO 2007/101862 describe how to make core human milk oligosaccharides optionally substituted by fucose or sialic acid using genetically modified *E. coli*.

The second aspect of this invention is a synthetic composition comprising an HMO, advantageously a neutral HMO, preferably a mixture of neutral HMOs, even more preferably a mixture of a fucosylated and a non-fucosylated neutral HMO as disclosed above in the first aspect, for use in the delayed increase in the abundance, particularly the relative abundance, of a *Bifidobacterium longum* and/or *Bifidobacterium bifidum*, in the microbiota in the gastro-intestinal tract of a non-infant, and thereby treating and/or preventing viral and/or bacterial infections (especially enteropathogenic infections), intestinal inflammatory diseases (especially IBS and IBD), allergies and gut-brain disorders and extra-intestinal diseases (especially obesity and type 2 diabetes).

The synthetic composition can be a pharmaceutical composition. The pharmaceutical composition can contain a pharmaceutically acceptable carrier, e.g. phosphate buffered saline solution, mixtures of ethanol in water, water and emulsions such as an oil/water or water/oil emulsion, as well as various wetting agents or excipients. The pharmaceutical composition can also contain other materials that do not produce an adverse, allergic or otherwise unwanted reaction when administered to non-infants. The carriers and other materials can include solvents, dispersants, coatings, absorption promoting agents, controlled release agents, and one or more inert excipients, such as starches, polyols, granulating agents, microcrystalline cellulose, diluents, lubricants, binders, and disintegrating agents. If desired, tablet dosages of the anti-infective compositions can be coated by standard aqueous or non-aqueous techniques.

The pharmaceutical compositions can be administered orally, e.g. as a tablet, capsule, or pellet containing a predetermined amount, or as a powder or granules containing a predetermined concentration or a gel, paste, solution, suspension, emulsion, syrup, bolus, electuary, or slurry, in an aqueous or non-aqueous liquid, containing a predetermined concentration. Orally administered compositions can include binders, lubricants, inert diluents, flavouring agents, and humectants. Orally administered compositions such as tablets can optionally be coated and can be formulated so as to provide sustained, delayed or controlled release of the mixture therein.

The pharmaceutical compositions can also be administered by rectal suppository, aerosol tube, naso-gastric tube or direct infusion into the GI tract or stomach.

The pharmaceutical compositions can also include therapeutic agents such as antiviral agents, antibiotics, probiotics, analgesics, and anti-inflammatory agents. The proper dosage of these compositions for a non-infant human can be determined in a conventional manner, based upon factors such immune status, body weight and age. In some cases, the dosage will be at a concentration similar to that found for the HMO, advantageously a neutral HMO, in human breast milk. The required amount would generally be in the range from about 200 mg to about 20 g per day, in certain embodiments from about 300 mg to about 15 g per day, from about 400 mg to about 10 g per day, in certain embodiments from about 500 mg to about 10 g per day, in certain embodiments from about 1 g to about 10 g per day. Appropriate dose regimes can be determined by conventional methods.

The synthetic composition can also be a nutritional composition. It can contain sources of protein, lipids and/or digestible carbohydrates and can be in powdered or liquid forms. The composition can be designed to be the sole source of nutrition or a nutritional supplement.

Suitable protein sources include milk proteins, soy protein, rice protein, pea protein and oat protein, or mixtures thereof. Milk proteins can be in the form of milk protein concentrates, milk protein isolates, whey protein or casein, or mixtures of both. The protein can be whole protein or hydrolysed protein, either partially hydrolysed or extensively hydrolysed. Hydrolysed protein offers the advantage of easier digestion which can be important for non-infants with inflamed GI tracts. The protein can also be provided in the form of free amino acids. The protein can comprise about 5% to about 30% of the energy of the nutritional composition, normally about 10% to 20%.

The protein source can be a source of glutamine, threonine, cysteine, serine, proline, or a combination of these amino acids. The glutamine source can be a glutamine dipeptide and/or a glutamine enriched protein. Glutamine can be included due to the use of glutamine by enterocytes as an energy source. Threonine, serine and proline are important amino acids for the production of mucin. Mucin coats the GI tract and can improve mucosal healing. Cysteine is a major precursor of glutathione, which is key for the antioxidant defences of the body.

Suitable digestible carbohydrates include maltodextrin, hydrolysed or modified starch or corn starch, glucose polymers, corn syrup, corn syrup solids, high fructose corn syrup, rice-derived carbohydrates, pea-derived carbohydrates, potato-derived carbohydrates, tapioca, sucrose, glucose, fructose, sucrose, lactose, honey, sugar alcohols (e.g., maltitol, erythritol, sorbitol), or mixtures thereof. Preferably the composition is free from lactose. Generally digestible carbohydrates provide about 35% to about 55% of the energy of the nutritional composition. Preferably the nutritional composition is free from lactose. A particularly suitable digestible carbohydrate is a low dextrose equivalent (DE) maltodextrin.

Suitable lipids include medium chain triglycerides (MCT) and long chain triglycerides (LCT). Preferably the lipid is a mixture of MCTs and LCTs. For example, MCTs can comprise about 30% to about 70% by weight of the lipids, more specifically about 50% to about 60% by weight. MCTs offer the advantage of easier digestion which can be important for non-infants with inflamed GI tracts. Generally the lipids provide about 35% to about 50% of the energy of the nutritional composition. The lipids can contain essential fatty acids (omega-3 and omega-6 fatty acids). Preferably these polyunsaturated fatty acids provide less than about 30% of total energy of the lipid source. Decreasing the levels of these polyunsaturated fatty acids is believed to decrease sensitivity to peroxidation; which can be beneficial for non-infants having inflammatory conditions.

Suitable sources of long chain triglycerides are rapeseed oil, sunflower seed oil, palm oil, soy oil, milk fat, corn oil, high oleic oils, and soy lecithin. Fractionated coconut oils are a suitable source of medium chain triglycerides. The lipid profile of the nutritional composition is preferably designed to have a polyunsaturated fatty acid omega-6 (n-6) to omega-3 (n-3) ratio of about 4:1 to about 10:1. For example, the n-6 to n-3 fatty acid ratio can be about 6:1 to about 9:1.

The nutritional composition preferably also includes vitamins and minerals. If the nutritional composition is intended to be a sole source of nutrition, it preferably includes a complete vitamin and mineral profile. Examples of vitamins include vitamins A, B-complex (such as B1, B2, B6 and B12), C, D, E and K, niacin and acid vitamins such as pantothenic acid, folic acid and biotin. Examples of minerals include calcium, iron, zinc, magnesium, iodine, copper, phosphorus, manganese, potassium, chromium, molybdenum, selenium, nickel, tin, silicon, vanadium and boron.

The nutritional composition can also include a carotenoid such as lutein, lycopene, zeaxanthin, and beta-carotene. The total amount of carotenoid included can vary from about 0.001 µg/ml to about 10 µg/ml. Lutein can be included in an amount of from about 0.001 µg/ml to about 10 µg/ml, preferably from about 0.044 µg/ml to about 5 g/ml of lutein. Lycopene can be included in an amount from about 0.001 µg/ml to about 10 µg/ml, preferably about 0.0185 mg/ml to about 5 g/ml of lycopene. Beta-carotene can comprise from about 0.001 µg/ml to about 10 mg/ml, for example about 0.034 µg/ml to about 5 µg/ml of beta-carotene.

The nutritional composition preferably also contains reduced concentrations of sodium; for example from about 300 mg/l to about 400 mg/l. The remaining electrolytes can be present in concentrations set to meet needs without providing an undue renal solute burden on kidney function. For example, potassium is preferably present in a range of about 1180 to about 1300 mg/l; and chloride is preferably present in a range of about 680 to about 800 mg/l.

The nutritional composition can also contain various other conventional ingredients such as preservatives, emulsifying agents, thickening agents, buffers, fibres and prebiotics (e.g. fructooligosaccharides, galactooligosaccharides), probiotics (e.g. *B. animalis* subsp. *lactis* BB-12, *B. lactis* HN019, *B. lactis* Bi07, *B. infantis* ATCC 15697, *L. rhamnosus* GG, *L. rhamnosus* HNOOI, *L. acidophilus* LA-5, *L. acidophilus* NCFM, *L. fermentum* CECT5716, *B. longum* BB536, *B. longum* AH1205, *B. longum* AH1206, *B. breve* M-16V, *L. reuteri* ATCC 55730, *L. reuteri* ATCC PTA-6485, *L. reuteri* DSM 17938), antioxidant/anti-inflammatory compounds including tocopherols, carotenoids, ascorbate/vitamin C, ascorbyl palmitate, polyphenols, glutathione, and superoxide dismutase (melon), other bioactive factors (e.g. growth hormones, cytokines, TFG-β), colorants, flavours, and stabilisers, lubricants, and so forth.

The nutritional composition can be in the form of a soluble powder, a liquid concentrate, or a ready-to-use formulation. The composition can be fed to a non-infant via a nasogastric tube or orally. Various flavours, fibres and other additives can also be present.

The nutritional compositions can be prepared by any commonly used manufacturing techniques for preparing nutritional compositions in solid or liquid form. For example, the composition can be prepared by combining various feed solutions. A protein-in-fat feed solution can be prepared by heating and mixing the lipid source and then adding an emulsifier (e.g. lecithin), fat soluble vitamins, and at least a portion of the protein source while heating and stirring. A carbohydrate feed solution is then prepared by adding minerals, trace and ultra trace minerals, thickening or suspending agents to water while heating and stirring. The resulting solution is held for 10 minutes with continued heat and agitation before adding carbohydrates (e.g. the HMOs and digestible carbohydrate sources). The resulting feed solutions are then blended together while heating and agitating and the pH adjusted to 6.6-7.0, after which the composition is subjected to high-temperature short-time processing during which the composition is heat treated, emulsified and homogenized, and then allowed to cool. Water soluble vitamins and ascorbic acid are added, the pH is adjusted to the desired range if necessary, flavours are added, and water is added to achieve the desired total solid level.

For a liquid product, the resulting solution can then be aseptically packed to form an aseptically packaged nutritional composition. In this form, the nutritional composition can be in ready-to-feed or concentrated liquid form. Alternatively the composition can be spray-dried and processed and packaged as a reconstitutable powder.

When the nutritional product is a ready-to-feed nutritional liquid, the total concentration of HMOs in the liquid, by weight of the liquid, is from about 0.0001% to about 2.0%, including from about 0.001% to about 1.5%, including from about 0.01% to about 1.0%. When the nutritional product is a concentrated nutritional liquid, the total concentration of HMOs in the liquid, by weight of the liquid, is from about 0.0002% to about 4.0%, including from about 0.002% to about 3.0%, including from about 0.02% to about 2.0%.

The synthetic composition comprising an HMO, advantageously a neutral HMO, preferably a mixture of neutral HMOs, even more preferably a mixture of a fucosylated and a non-fucosylated neutral HMO disclosed above, can also be in a unit dosage form such as a capsule, tablet or sachet. For example, the synthetic composition can be in a tablet form comprising the HMOs, and one or more additional components to aid formulation and administration, such as diluents, excipients, antioxidants, lubricants, colorants, binders, disintegrants and the like.

Suitable diluents, excipients, lubricants, colorants, binders, and disintegrants include polyethylene, polyvinyl chloride, ethyl cellulose, acrylate polymers and their copolymers, hydroxyethyl-cellulose, hydroxypropylmethyl-cellulose (HPMC), sodium carboxymethylcellulose, polyhydroxyethyl methylacrylate (PHEMA), polyvinyl alcohol (PVA), polyvinyl pyrrolidone (PVP), polyethylene oxide (PEO), or polyacrylamide (PA), carrageenan, sodium alginate, polycarbophil, polyacrylic acid, tragacanth, methyl cellulose, pectin, natural gums, xanthan gum, guar gum, karaya gum, hypromellose, magnesium stearate, microcrystalline cellulose, and colloidal silicon dioxide. Suitable antioxidants are vitamin A, carotenoids, vitamin C, vitamin E, selenium, flavonoids, polyphenols, lycopene, lutein, lignan, coenzyme Q10 ("CoQ10") and glutathione.

The unit dosage forms, especially those in sachet form, can also include various nutrients including macronutrients.

A first target group of this invention includes healthy non-infants. Their ingestion of one or more HMOs, preferably a mixture of neutral HMOs, even more preferably a mixture of a fucosylated and a non-fucosylated neutral HMO, for a period of at least 14 days, preferably more than 14 days, will affect the composition of the intestinal microbiota by preferentially promoting the growth of *Bifidobacterium longum* and/or *Bifidobacterium bifidum*, which will increase its relative and absolute abundance in their gastrointestinal tract.

A second target group of this invention includes non-infants with an enteropathogenic infection. Their ingestion of one or more HMOs, preferably a mixture of neutral HMOs, even more preferably a mixture of a fucosylated and a non-fucosylated neutral HMO, for a period of at least 14 days, preferably more than 14 days, will increase the intestinal abundance of *Bifidobacterium longum* and/or *Bifidobacterium bifidum*, and as a result, induce a favourable immune response against the enteropathogenic microorganism, inhibiting or treating infection.

A third target group for this invention includes obese non-infants, and/or lean or obese non-infants diagnosed with type 2 diabetes. Their ingestion of one or more HMOs, preferably a mixture of neutral HMOs, even more preferably a mixture of a fucosylated and a non-fucosylated neutral HMO, for a period of at least 14 days, preferably more than 14 days, increases the intestinal abundance of *Bifidobacterium longum* and/or *Bifidobacterium bifidum*, and as a result, improves intestinal permeability and/or increases insulin sensitivity, hence reducing the pathological conditions of type 2 diabetes and/or obesity.

A fourth target group for this invention includes non-infants diagnosed with intestinal diseases such as IBD and IBS and immune-related conditions such as allergies. Their ingestion of one or more HMOs, preferably a mixture of neutral HMOs, even more preferably a mixture of a fucosylated and a non-fucosylated neutral HMO, for a period of at least 14 days, preferably more than 14 days, increases the intestinal abundance of *Bifidobacterium longum* and/or *Bifidobacterium bifidum*, and as a result, contributes to immunomodulation by inducing an anti-inflammatory immune response, hence improving symptoms.

The third aspect of this invention provides a method for increasing the abundance, particularly the relative abundance, of *Bifidobacterium longum* and/or *Bifidobacterium bifidum*, in the microbiota in the gastro-intestinal tract of a non-infant, the method comprising enterally, preferably orally, administering to the non-infant human for a period of at least 14 days, preferably more than 14 days:
- an effective amount of one or more HMOs, or
- a synthetic composition comprising an effective amount of one or more HMOs.

The fourth aspect of this invention is a method for the prophylaxis or treatment of an enteropathogenic infection in a non-infant, the method comprising enterally, preferably orally, administering to the non-infant human for a period of at least 14 days, preferably more than 14 days:
- an amount of one or more HMOs, or
- a synthetic composition comprising an amount of one or more HMOs, effective to increase the abundance, particularly the relative abundance, of *Bifidobacterium longum* and/or *Bifidobacterium bifidum*, in the microbiota in the gastro-intestinal tract of the non-infant human.

The fifth aspect of this invention provides a method for the prophylaxis or treatment of a non-infant in an obese state and/or having type 2 diabetes, the method comprising enterally, preferably orally, administering to the non-infant human for a period of at least 14 days, preferably more than 14 days:
- an amount of one or more HMOs, or
- a synthetic composition comprising an amount of one or more HMOs, effective to increase the abundance, particularly the relative abundance, of *Bifidobacterium longum* and/or *Bifidobacterium bifidum*, in the microbiota in the gastro-intestinal tract of the non-infant, to sufficiently improve intestinal permeability and/or increase insulin sensitivity.

The sixth aspect of this invention provides a method for the prophylaxis or treatment of a non-infant human having an inflammation related gastro-intestinal condition or an immune related condition such as allergy, the method comprising enterally, preferably orally, administering to the non-infant human for a period of at least 14 days, preferably more than 14 days:
- an amount of one or more HMOs, or
- a synthetic composition comprising an amount of one or more HMOs, effective to increase the abundance, particularly the relative abundance, of *Bifidobacterium longum* and/or *Bifidobacterium bifidum*, in the microbiota in the gastro-intestinal tract of the non-infant, to sufficiently induce an anti-inflammatory immune response. The gastro-intestinal condition is preferably intestinal bowel disease or irritable bowel syndrome.

The seventh aspect of this invention is a method for the prophylaxis or treatment of a non-infant human having a gut-brain disorder, for example stress, anxiety or depressive like behaviour, the method comprising enterally, preferably orally, administering to the non-infant human for a period of at least 14 days, preferably more than 14 days:
- an amount of one or more HMOs, or
- a synthetic composition comprising an amount of one or more HMOs, effective to increase the abundance, particularly the relative abundance, of *Bifidobacterium longum* and/or *Bifidobacterium bifidum* in the microbiota in the gastro-intestinal tract of the non-infant human.

In the third to seventh aspects of the invention, the administration of one or more HMOs or a synthetic composition comprising one or more HMOs lasts at least 14 days, but preferably more than 14 days, such as three weeks, four weeks, five weeks or even longer.

The eight aspect of this invention is method for modulating the bifidobacterial composition of the gastrointestinal microbiota of a non-infant human, the method comprising enterally, preferably orally, administering to the non-infant human:
(a) in a first step for a period of 14 days or less:
- an effective amount of one or more HMOs, or
- a synthetic composition comprising an effective amount one or more HMOs,
to increase the abundance, particularly the relative abundance, of a *Bifidobacterium* of the *Bifidobacterium adolescentis* phylogenetic group in the microbiota in the gastro-intestinal tract of the non-infant human, and
(b) in a second step for an additional period:
- an effective amount of one or more HMOs, or
- a synthetic composition comprising an effective amount one or more HMOs,
to increase the abundance, particularly the relative abundance, of *Bifidobacterium longum* and/or *Bifidobacterium bifidum* in the microbiota in the gastro-intestinal tract of the non-infant human, wherein the period of the first step and the additional period of the second step together are at least 14 days, preferably more than 14 days, such as three weeks, four weeks, five weeks or even longer.

In the third to eight aspects of therapeutic and prophylactic treatment of the invention, the HMO is advantageously a neutral HMO. The one or more neutral HMO can preferably be one or more fucosylated HMOs or one or more non-fucosylated HMOs. In one embodiment, the neutral HMO is a mixture of neutral HMOs, more preferably a mixture comprising, essentially consisting of or consisting of a fucosylated and a non-fucosylated neutral HMO. Particularly, the mixture contains, essentially consists of or consists of a fucosylated neutral HMO selected from the list consisting of 2'-FL, 3-FL, DFL, LNFP-I, LNFP-II, LNFP-III, LNFP-V, LNFP-VI, LNDFH-I, LNDFH-II, LNDFH-III, FLNH-I, FLNH-II, FLNnH, FpLNH-I and F-pLNnH II, and a non-fucosylated neutral HMO selected from the list consisting of LNT, LNnT, LNH, LNnH, pLNH and pLNnH. Especially, the mixture contains, essentially consists of or consists of a fucosylated neutral HMO selected from the list consisting of 2'-FL, 3-FL and DFL, and a non-fucosylated neutral HMO selected from the list consisting of LNT and LNnT, advantageously the mixture comprises, essentially consists of or consists of i) 2'-FL and LNnT, ii) 2'-FL and LNT or iii) 2'-FL, LNT and LNnT.

For increasing the abundance of *Bifidobacterium longum* and/or *Bifidobacterium bifidum*, in the gastro-intestinal tract of a non-infant human, the amount of HMO(s) required to be administered will vary depending upon factors such as the risk and severity of the obesity, type 2 diabetes, the inflammatory gastrointestinal condition, the allergy, the gut brain disorder or the enteropathogenic infection, age, the form of the composition, and other medications being administered. However, the required amount can be readily set by a medical practitioner and would generally be in the range from about 10 mg to about 20 g per day, in certain embodiments from about 10 mg to about 15 g per day, from about 100 mg to about 10 g per day, in certain embodiments from about 500 mg to about 10 g per day, in certain embodiments from about 1 g to about 7.5 g per day. An appropriate dose can be determined based on several factors, including, for example, body weight and/or condition, the severity of the of type 2 diabetes, the inflammatory gastrointestinal condition or the enteropathogenic infection, being treated or prevented, other ailments and/or diseases, the incidence and/or severity of side effects and the manner of administration. Appropriate dose ranges may be determined by methods known to those skilled in the art. In one embodiment, the daily amount of HMO(s) is the same during the entire treatment period. In other embodiment, during about the first 14 days of treatment, the dosing can be higher (for example 200 mg to 20 g per day, preferably 500 mg to 15 g per day, more preferably 1 g to 10 g per day, in certain embodiments 2.5 g to 7.5 g per day), and in the period afterwards the dosing can be reduced (for example, 10 mg to 10 g per day, preferably 100 mg to 7.5 g per day, more preferably 500 mg to 5 g per day, in certain embodiments 1 g to 2.5 g per day).

In a ninth aspect, this invention relates to use of:
an HMO, advantageously a neutral HMO, as disclosed in the first aspect, or
a synthetic composition containing an HMO, advantageously a neutral HMO, as described in the second aspect,
in increasing the abundance of *Bifidobacterium longum* and/or *Bifidobacterium bifidum*, in the gastro-intestinal tract of a non-infant human in a delayed manner, preferably to treat or prevent in the non-infant human:
an enteropathogenic infection,
type 2 diabetes and/or obesity,
impaired gut barrier function,
brain-gut disorders,
allergy, and/or
an inflammation related to gastro-intestinal condition.

In a yet further aspect, this invention relates to a kit-of-parts comprising a first dosage of
a human milk oligosaccharide, advantageously a neutral HMO, as disclosed in the first aspect, or
a synthetic composition comprising a human milk oligosaccharide, advantageously a neutral HMO, as described in the second aspect,
wherein the first dosage comprises at least 14 daily doses of said human milk oligosaccharide or said composition.

In particular, the neutral HMO can preferably be one or more fucosylated HMOs or one or more non-fucosylated HMOs. In one embodiment, the neutral HMO is a mixture neutral HMOs, even preferably a mixture comprising, essentially consisting of or consisting of a fucosylated and a non-fucosylated neutral HMO. Particularly, the mixture contains, essentially consisting of or consists of a fucosylated neutral HMO selected from the list consisting of 2'-FL, 3-FL, DFL, LNFP-I, LNFP-II, LNFP-III, LNFP-V, LNFP-VI, LNDFH-I, LNDFH-II, LNDFH-III, FLNH-I, FLNH-II, FLNnH, FpLNH-I and F-pLNnH II, and a non-fucosylated neutral HMO selected from the list consisting of LNT, LNnT, LNH, LNnH, pLNH and pLNnH. Especially, the mixture contains, essentially consists of or consists of a fucosylated neutral HMO selected from the list consisting of 2'-FL, 3-FL and DFL, and a non-fucosylated neutral HMO selected from the list consisting of LNT and LNnT, advantageously the mixture comprises, essentially consists of or consist of i) 2'-FL and LNnT, ii) 2'-FL and LNT or iii) 2'-FL, LNT and LNnT.

The at least 14 daily doses are preferably in the form of a unit dosage comprising a daily dose of HMO.

Preferably, the daily dose of the first dosage preferably corresponds to an amount of the human milk oligosaccharide in the range from 200 mg to 20 g, such as from 500 mg to 15 g, from 1 g to 10 g or 2 g to 8 g.

The kit-of-parts may further comprise a second dosage of
a human milk oligosaccharide, advantageously a neutral HMO, as disclosed in the first aspect, or
a synthetic composition comprising a human milk oligosaccharide, advantageously a neutral HMO, as described in the second aspect,
wherein the second dosage comprises at least 14 daily doses of said human milk oligosaccharide or said composition.

The daily dose of the second dosage may be the same or different than that of the first dosage. In one embodiment, the amount of the human milk oligosaccharide as daily dose in the second dosage may be decreased compared to that in the first dosage; in another embodiment, the amount of the human milk oligosaccharide as daily dose in the first and second dosage may be equal; in another embodiment, the amount of human milk oligosaccharide as daily dose in the second dosage may be higher than that the first dosage. Preferably, the amount of the human milk oligosaccharide in the second dosage may be in the range from 10 mg to 10 g, such from 100 mg to 7.5, 500 mg to 5 g or from 1 g to 2.5 g, per day.

The kit-of parts can be used for the delayed increase in the abundance, particularly the relative abundance, of a *Bifidobacterium longum* and/or *Bifidobacterium bifidum*, in the microbiota in the gastro-intestinal tract of non-infant humans. Preferably, the non-infant human is diagnosed with one or more of the following:
an enteropathogenic infection,
type 2 diabetes and/or obesity,
impaired gut barrier function,
brain-gut disorders,
allergy,
an inflammation related to a gastro-intestinal condition.

Whilst the invention has been described with reference to a preferred embodiment, it will be appreciated that various modifications are possible within the scope of the invention.

EXAMPLES

The working example described herein are for illustration purposes only and should not be considered as limiting.

Example 1

A total of 100 male and female healthy adults are recruited to participate in the study. After a screening visit and run-in period of 1-2 weeks, the participants are selected and randomized into ten groups, each of 10 subjects. One group is administered a placebo product containing 2 grams of glucose. The remaining 9 groups are administered treatment product containing a) 20 g of 2'-FL, b) 10 g of 2'-FL, c) 5 g of 2'-FL, d) 20 g of LNnT, e) 10 g of LNnT, f) 5 g of LNnT, g) 20 g of a 2:1 mixture of 2'-FL and LNnT, h) 10 g of a 2:1 mixture of 2'-FL and LNnT, and i) 5 g of a 2:1 mixture of 2'-FL and LNnT for 4 weeks. The placebo and treatment products are in powder form in a unit dosage container.

The healthy adults are eligible to participate if they are at an age between 18-60 years. All recruited participants are able and willing to understand and comply with the study procedures. Participants are excluded if: they had participated in a clinical study one month prior to screening visit; they had abnormal results in the screening tests which were clinically relevant for study participation; they are suffering for a severe disease such as malignancy, diabetes, severe coronary disease, kidney disease, neurological disease, or severe psychiatric disease or any condition which could confound the results of the study; used highly dosed probiotic supplements (yoghurt allowed) for 3 months prior to the study; they consumed antibiotic drugs 6 months prior to the study; they consumed on a regular basis any medication that might have interfered with symptom evaluation 2 weeks prior to the study; and are pregnant or lactating.

At the screening visit, medical history and concomitant medication is registered and a blood sample for safety analyses is collected. A faecal sample kit is distributed. Participants are instructed to keep their samples in the freezer until the next visit.

At the second visit, eligibility criteria are checked and eligible subjects are randomised to the ten arms in the trial (treatment groups and placebo group). The faecal samples are collected and equipment for new samples are distributed. Participants are familiarised with an interactive internet enabled system which recorded data daily and are provided with either treatment or control products. Subjects are reminded not to change their usual diet during the study. Blood samples are collected for biomarker studies. The faecal samples are stored at −80° C. until analysis.

The study runs for 4 weeks with the participants consuming either a placebo or a treatment product daily. Participants are instructed to consume the products in the morning with breakfast. Compliance is monitored through the interactive internet enabled system.

The participants also use the system to record:
Bristol Stool Form Scale (BSFS) information.
Symptom information such as abdominal pain, abdominal discomfort, abdominal cramping, abdominal bloating, and abdominal fullness.
Additional, Gastrointestinal Symptom Rating Scale (GSRS) information.

This questionnaire includes 15 items covering five dimensions (abdominal pain, indigestion, reflux, diarrhoea, constipation) and uses a seven-graded Likert scale.

After 2 weeks, each participant has a visit with the medical team. Faecal samples and blood samples are collected. The faecal samples are stored at −80° C. until analysis. Equipment for new samples are distributed. Subjects are reminded not to change their usual diet during the study.

After 4 weeks, each participant has an exit visit with the medical team. Faecal samples and blood samples are collected. The faecal samples are stored at −80° C. until analysis.

Blood samples are analysed simultaneously in a multiplexing format on an electrochemiluminescence platform. The following analytes are included in the panel: BUN, LDL cholesterol, HDL cholesterol, iron, triglycerides, ApoA1, ApoB, insulin, FFAs, glucagon, IL-10, IL-6 and TNF-α.

To assess the microbiota profile, DNA is extracted from the faecal samples using a 96-well PowerSoil DNA Isolation Kit (MO-BIO). A minimum of one sample-well per plate is kept empty to serve as a negative control during PCR. PCR is done with the forward primer S-D-Bact-0341-b-S-17 and reverse primer S-D-Bact-0785-a-A-21 with Illumina adapters attached (Klindworth et al. *Nucleic Acids Res.* 41, el (2013)). These are universal bacterial 16S rDNA primers, which targeted the V3-V4 region. The following PCR program is used: 98° C. for 30 sec, 25× (98° C. for 10 s, 55° C. for 20 s, 72° C. for 20 s), 72° C. for 5 min. Amplification is verified by running the products on a 1% agarose gel. Barcodes are added in a nested PCR using the Nextera Index Kit V2 (Illumina) with the following PCR program: 98° C. for 30 sec, 8× (98° C. for 10 s, 55° C. for 20 s, 72° C. for 20 s), 72° C. for 5 min. Attachment of primers is verified by running the products on a 1% agarose gel. Products from the nested PCR are normalized using the SequalPrep Normalization Plate Kit and pooled. Pooled libraries are concentrated by evaporation and the DNA concentration of pooled libraries is measured on a Qubit fluorometer using the Qubit High Sensitivity Assay Kit (Thermo Fisher Scientific). Sequencing is done on a MiSeq desktop sequencer using the MiSeq Reagent Kit V3 (Illumina) for 2×300 bp paired-end sequencing. The 64-bit version of USEARCH (Edgar *Nature Methods* 10, 996 (2013)) is used for bioinformatical analysis of the sequence data.

To assess the *Bifidobacterium* community, ITS profiling of DNA samples is performed.

The results from the profiling of the *Bifidobacterium* community shows that, for the first 2 weeks, the abundance of *B. adolescentis* increases when consuming a single HMO, where the abundance of *B. pseudocatenulatum* increases when consuming a mix of two HMOs. Both *B. adolescentis* and *B. pseudocatenulatum* are members of the *B. adolescentis* phylogenetic group. At 4 weeks, the abundance of members of the *B. adolescentis* phylogenetic group reduce while the abundance of *Bifidobacterium longum* and/or *Bifidobacterium bifidum* increase. It can be seen that oral ingestion of the HMOs for more than 14 days clearly increases the abundance of *Bifidobacterium longum* and/or *Bifidobacterium bifidum* in the microbiota of healthy adults, as well as their relative abundance compared to the totality of other *Bifidobacterium* species.

Example 2

The impact of the HMOs on microbiota is investigated in the M-SHIME® in vitro gastrointestinal model (Prodigest). The typical reactor setup of the M-SHIME® consists of a succession of five reactors simulating the different parts of the human gastrointestinal tract. The first two reactors simulate different steps in food uptake and digestion in the stomach and small intestine. The last three compartments simulate the large intestine. The retention time and pH of the different vessels are chosen to resemble in vivo conditions in the different parts of the colon. Upon inoculation with faecal microbiota, these reactors simulate the ascending, transverse and descending colon. After a two-week adaptation of the microbial communities in the different regions of the colon, a representative microbial community is established in the three colon compartments, which differs both in composition and functionality in the different colon regions.

Further, porcine mucin is included in the reactors simulating the colon to take into account the colonisation of the mucous layer. Thus the M-SHIME® permits culturing both the luminal and mucous-associated microbial community over periods of several weeks.

The M-SHIME® is run in four stages:
1. Stabilisation: After inoculation of the reactors with a fresh faecal sample taken from a healthy adult, a two-week stabilisation period allows the microbial community to differentiate in the different reactors depending on the local environmental conditions. During this period the basic nutritional matrix is provided to support the maximum diversity of the gut microbiota originally present in the faecal inoculum.
2. Control: During this two-week period, a standard nutrient matrix is dosed into the model for a period of 14 days. The baseline microbial community composition and activity in the different reactors is determined by analysis of samples and is used as a reference.
3. Treatment: The SHIME system is operated under normal conditions for 3 weeks, but with the standard nutrient matrix supplemented with the HMOs. The HMOs tested are 2'-FL, LNnT and a 4:1 mix of 2'-FL and LNnT.

4. Washout: During this two-week period, the SHIME system is again run with the standard nutrient matrix only.

Sample of the liquids in each reactor are collected regularly and are analysed for microbial metabolites and the composition of the resident microbial community. In particular, the bifidobacteria composition is analysed using ITS profiling.

The results from the profiling of the *Bifidobacterium* community shows that, for the first 2 weeks, the abundance of *B. adolescentis* increases when consuming HMOs. However, by week 3, the relative abundance of members of the *B. adolescentis* phylogenetic group reduces while the abundance and relative abundance of *Bifidobacterium longum* and/or *Bifidobacterium bifidum* increases. It can be seen that feeding the M-SHIME® with HMOs for more than 14 days increases the abundance of *Bifidobacterium longum* and/or *Bifidobacterium bifidum* in the microbiota from healthy adults, as well as their relative abundance compared to the totality of other *Bifidobacterium* species.

The invention claimed is:

1. A method comprising:
   selecting an effective amount of one or more human milk oligosaccharides (HMOs) chosen from the group consisting of 2'-fucosyllactose (2'-FL), 3-fucosyllactose (3-FL), difucosyllactose (DFL), lacto-N-fucopentaose I (LNFP-I), lacto-N-tetraose (LNT), lacto-N-neotetraose (LNnT), and combinations thereof, the amount effective for increasing a relative abundance of *Bifidobacterium adolescentis* in the gastrointestinal microbiota of a non-infant human;
   administering the effective amount of the selected HMOs to the non-infant human for a treatment period of at least 14 days thereby increasing the relative abundance of *Bifidobacterium adolescentis* and subsequently increasing the relative abundance of *Bifidobacterium longum* and/or *Bifidobacterium bifidum* in the gastrointestinal microbiota of the non-infant human; and
   reducing the likelihood of the non-infant human experiencing one or more symptoms of a gastrointestinal-related disorder by the administration.

2. The method of claim 1, wherein the gastrointestinal-related disorder comprises one or more of an enteropathogenic infection, an inflammation-related gastrointestinal condition, an immune-related condition, a gut-brain disorder, and an obesity-related condition.

3. The method of claim 2, further comprising improving intestinal permeability and/or increasing insulin sensitivity in the non-infant human experiencing an obesity-related condition comprising type 2 diabetes and/or obesity, by increasing the relative abundance of one or more of the adult-type species of bifidobacteria selected from *Bifidobacterium adolescentis*, *Bifidobacterium longum*, and and/or *Bifidobacterium bifidum* in the gastrointestinal microbiota of the non-infant human during the treatment period.

4. The method of claim 2, further comprising inducing an anti-inflammatory immune response in the non-infant human experiencing an inflammation-related gastrointestinal condition comprising one or more of Inflammatory Bowel Disease ("IBD"), Irritable Bowel Syndrome ("MS"), and an allergy, by increasing the relative abundance of one or more of the adult-type species of bifidobacteria selected from *Bifidobacterium adolescentis*, *Bifidobacterium longum*, and *Bifidobacterium bifidum* in the gastrointestinal microbiota of the non-infant human during the treatment period.

5. The method of claim 2, further comprising reducing one or more of the stress, anxiety, and/or the depressive-like behaviour in the non-infant human experiencing a gut-brain disorder comprising one or more of stress, anxiety, and/or depressive-like behaviour, by increasing the relative abundance of one or more of the adult-type species of bifidobacteria selected from *Bifidobacterium adolescentis*, *Bifidobacterium longum*, and *Bifidobacterium bifidum* in the gastrointestinal microbiota of the non-infant human during the treatment period.

6. The method of claim 1 wherein the treatment period is at least 21 days.

7. A method for modulating the bifidobacterial composition of the gastrointestinal microbiota of a non-infant human, the method comprising:
   selecting an effective amount of one or more human milk oligosaccharides (HMOs) chosen from the group consisting of 2'-fucosyllactose (2'-FL), 3-fucosyllactose (3-FL), difucosyllactose (DFL), lacto-N-fucopentaose I (LNFP-I), lacto-N-tetraose (LNT), lacto-N-neotetraose (LNnT), and combinations thereof, the amount effective for increasing a relative abundance of *Bifidobacterium adolescentis* in the gastrointestinal microbiota of the non-infant human; and
   enterally administering to the non-infant human
   (a) in a first dosage for a first treatment period of 14 days or less: the selected effective amount of the one or more HMOs and increasing the relative abundance of *Bifidobacterium adolescentis* in the gastrointestinal microbiota of the non-infant human during the first treatment period, and
   (b) in a second dosage for a second treatment period: the selected effective amount of the one or more HMOs and increasing the relative abundance of *Bifidobacterium longum* and/or *Bifidobacterium bifidum* in the gastrointestinal microbiota of the non-infant human during the second treatment period.

8. The method of claim 7, wherein the first dosage comprises at least 14 daily doses of the selected effective amount of the one or more HMOs.

9. The method of claim 8, wherein the daily dose of the first dosage corresponds to an amount of the human milk oligosaccharide in the range from 2 g to 15 g.

10. The method of claim 8 wherein the second dosage comprises at least 14 daily doses of the selected effective amount of the one or more HMOs.

11. The method of claim 10, wherein the daily dose of the second dosage corresponds to an amount of the human milk oligosaccharide in the range from 1 g to 10 g.

12. The method of claim 7, wherein the non-infant human is diagnosed with one or more of the following:
   an enteropathogenic infection,
   an obesity-related condition comprising type 2 diabetes and/or obesity,
   an impaired gut barrier function,
   a brain-gut disorder,
   an allergy, and
   an inflammation related to a gastrointestinal condition.

13. The method of claim 7, further comprising administering with the selected effective amount of the one or more HMOs, one or more additional HMOs selected from the group consisting of 3'-sialyllactose (3'-SL) and 6'-sialyllactose (6'-SL).

14. The method of claim 7, wherein the selected effective amount of the one or more HMOs comprises a mixture of at least one fucosylated HMO selected from 2'-FL, 3-FL, LNFP-I, and DFL; and at least one non-fucosylated HMO selected from LNT and LNnT.

15. The method of claim 12, further comprising improving intestinal permeability and/or increasing insulin sensitivity in the non-infant human experiencing an obesity-related condition comprising type 2 diabetes and/or obesity, by increasing the relative abundance of one or more of the adult-type species of bifidobacteria selected from *Bifidobacterium adolescentis*, *Bifidobacterium longum*, and and/or *Bifidobacterium bifidum* in the gastrointestinal microbiota of the non-infant human during the first and/or second treatment period.

16. The method of claim 12, further comprising inducing an anti-inflammatory immune response in the non-infant human experiencing an inflammation-related gastrointestinal condition comprising one or more of Inflammatory Bowel Disease ("IBD"), Irritable Bowel Syndrome ("IBS"), and an allergy, by increasing the relative abundance of one or more of the adult-type species of bifidobacteria selected from *Bifidobacterium adolescentis*, the *Bifidobacterium longum*, and *Bifidobacterium bifidum* in the gastrointestinal microbiota of the non-infant human during the first and/or second treatment period.

17. The method of claim 12, further comprising reducing one or more of the stress, anxiety, and/or the depressive-like behaviour in the non-infant human experiencing a gut-brain disorder comprising one or more of stress, anxiety, and/or depressive-like behaviour, by increasing the relative abundance of one or more of the adult-type species of bifidobacteria selected from *Bifidobacterium adolescentis*, *Bifidobacterium longum*, and *Bifidobacterium bifidum* in the gastrointestinal microbiota of the non-infant human during the first and/or second treatment period.

18. The method of claim 1, further comprising administering with the selected effective amount of the one or more HMOs, one or more additional HMOs selected from the group consisting of 3'-sialyllactose (3'-SL) and 6'-sialyllactose (6'-SL).

19. The method of claim 1, wherein the selected effective amount of the one or more HMOs comprises a mixture of at least one fucosylated HMO selected from 2'-FL, 3-FL, LNFP-I, and DFL; and at least one non-fucosylated HMO selected from LNT and LNnT.

20. The method of claim 1, wherein a daily dose of the selected effective amount of the one or more HMOs corresponds to an amount of the human milk oligosaccharide in the range from 1 g to 15 g.

* * * * *